United States Patent

Narbeshuber et al.

Patent Number: 6,046,130
Date of Patent: Apr. 4, 2000

[54] CATALYST AND SIDE-CHAIN ALKYLATION THEREWITH

[75] Inventors: Thomas Narbeshuber, Ludwigshafen; Georg Heinrich Grosch, Bad Dürkheim; Michael Trefzer, Otterstadt; Eugen Gehrer, Ludwigshafen; Michael Baier, Mannheim, all of Germany

[73] Assignee: BASF Aktiengesellschaft, Ludwigshafen, Germany

[21] Appl. No.: 09/055,673

[22] Filed: Apr. 7, 1998

[30] Foreign Application Priority Data

Apr. 11, 1997 [DE] Germany .......................... 197 15 203

[51] Int. Cl.[7] .............................. B01J 23/02; B01J 23/00; B01J 23/40; B01J 23/58; B01J 23/72
[52] U.S. Cl. .......................... 502/340; 502/325; 502/327; 502/328; 502/329; 502/330; 502/331; 502/332; 502/340; 502/341; 502/344; 502/351; 502/524
[58] Field of Search ..................................... 502/524, 330, 502/325, 327, 328, 329, 331, 332, 340, 341, 344, 351

[56] References Cited

U.S. PATENT DOCUMENTS

| | | | |
|---|---|---|---|
| 2,556,280 | 6/1951 | Kearby | 502/524 |
| 3,928,238 | 12/1975 | Koberstein et al. | 502/330 |
| 4,220,560 | 9/1980 | Anquetil et al. | 502/524 |
| 4,471,070 | 9/1984 | Siefert et al. | 502/524 |
| 4,480,050 | 10/1984 | Brennan | 502/330 |
| 4,492,677 | 1/1985 | Yoo et al. | 502/524 |
| 4,522,937 | 6/1985 | Yoo et al. | 502/524 |
| 4,618,597 | 10/1986 | Fiato et al. | 502/524 |
| 4,914,250 | 4/1990 | Smith | 585/452 |
| 4,922,054 | 5/1990 | Smith | 585/452 |
| 4,952,549 | 8/1990 | Immel et al. | 502/333 |
| 5,399,792 | 3/1995 | Demmering | 568/864 |
| 5,525,211 | 6/1996 | Sudhakar et al. | 502/322 |
| 5,736,114 | 4/1998 | Barthe et al. | 423/213.2 |

FOREIGN PATENT DOCUMENTS

| | | |
|---|---|---|
| 439 679 | 8/1991 | European Pat. Off. .......... C07C 2/72 |
| 1117595 | 6/1968 | United Kingdom . |
| 1550873 | 8/1979 | United Kingdom . |
| 88/04956 | 7/1988 | WIPO . |

OTHER PUBLICATIONS

Advanced inorganic Chemistry, Fifth Ed., F. Albert Cottonn and Geoffrey Wilkinson, p. 125 (Month Not Availabe).
Japanese Abstract A2–05163171 Jun. 29, 1993.

*Primary Examiner*—Mark L. Bell
*Assistant Examiner*—Patricia L. Hailey
*Attorney, Agent, or Firm*—Keil & Weinkauf

[57] ABSTRACT

The catalyst comprising at least one alkali metal on a spinel or inverse spinel as carrier may be doped with at least one compound of an alkali metal and/or alkaline earth metal, where the alkali metal/carrier ratio by weight is from 0.01 to 5 and, when a dopant is present, the dopant/carrier ratio by weight is from 0.01 to 5.

The spinel therein has formula (I) and the inverse spinel has formula (II)

$$AB_2X_4 \qquad (I)$$

$$B(AB)X_4 \qquad (II)$$

where
  A is divalent metal,
  B is tri- or tetravalent metal,
  X is O, S, Se, halogen, pseudohalogen,
the charges being balanced, and A preferably being selected from Mg, Cr, Fe, Zn, Mn, Co, Ni, Cu, Cd, Sn and mixtures thereof, and B being selected from Al, Ga, In, Fe, V, Cr, Ti, Pb, Mn, Co, Rh, Ni, Si and mixtures thereof, and X being O.

5 Claims, No Drawings

CATALYST AND SIDE-CHAIN ALKYLATION THEREWITH

The invention relates to a catalyst, to its use in reactions catalyzed by strong bases, and to a process for the side-chain alkenylation or side-chain alkenylation of alkylaromatic or alkylalicyclic compounds with olefins or diolefins.

Side-chain alkylation, especially of aromatic compounds which have an acidic proton in the a position of the side chain, in the presence of catalysts is known.

EP-B-0 439 679 describes a process for the alkylation of alkylaromatic hydrocarbons. The reaction takes place in the presence of a catalyst consisting of activated alumina doped with magnesium hydroxide and potassium metal. Also used in place of magnesium hydroxide were calcium hydroxide, barium hydroxide or magnesium oxide. Impregnation with potassium hydride is also described.

U.S. Pat. No. 4,914,250 relates to a process for the side-chain alkylation of aromatic compounds. The catalyst employed in this case was diatomaceous earth which was present in the reaction mixture together with potassium or NaK and traces of water.

U.S. Pat. No. 4,922,054 likewise relates to a process for the side-chain alkylation of aromatic compounds, in which diatomaceous earth was likewise employed as catalyst and was present in the reaction mixture together with NaK and potassium oxide. Rubidium oxide was also used in place of potassium oxide. Potassium metal was also employed in place of NaK.

JP-A2-05163171 relates to the preparation of alkenylbenzene and its derivatives. The catalyst used comprises an alkali metal and a potassium carbonate salt and/or KOH, which are dispersed in the presence of an olefin and/or diolefin. Sodium metal is preferably employed as alkali metal, and $K_2CO_3$, $KHCO_3$ or $KNaCO_3$ is preferably employed as potassium carbonate salt.

These previously disclosed catalysts are inadequately effective for many applications. On the one hand the catalysts disclosed to date have low activity, ie. the space-time yield is very low. In addition, with high conversions and longer use times, they form unwanted secondary products from the primary products initially obtained. For example, in the side-chain alkylation of toluene with propene the formation of isobutylbenzene is followed by cyclization to methylindane and by dimerization of the olefin, for example to form methylpentene from propene. In addition, the useful life of the catalysts described is limited. As the reaction time increases, the catalysts lose their activity and in some cases their spectrun of byproducts alters.

It is an object of the present invention to provide a catalyst for side-chain alkylation which avoids the disadvantages of the known catalysts and has high activity, selectivity and useful life.

We have found that this object is achieved by providing a catalyst comprising at least one alkali metal on a spinel of the formula (I) or inverse spinel of the formula (II) as carrier, which may be doped with at least one compound of an alkali metal and/or alkaline earth metal, where the alkali metal/carrier ratio by weight is from 0.01 to 5 and, when a dopant is present, the dopant/carrier ratio by weight is from 0.01 to 5.

We have furthermore found that the object is achieved by using this catalyst in reactions catalyzed by strong bases, preferably for the side-chain alkylation or side-chain alkenylation of alkylaromatic or alkylalicyclic compounds with olefins or diolefins, for double-bond isomerization of olefins or for dimerization of olefins.

The object is furthermore achieved by way of example by providing a process for the side-chain alkylation or side-chain alkenylation of alkylaromatic or alkylalicyclic compounds by reaction with olefins or diolefins, the reaction being carried out in the presence of a catalyst defined above.

It has been found according to the invention that catalysts based on spinels or inverse spinels have excellent properties in side-chain alkylation.

The alkali metal/carrier ratio in this connection is preferably from 0.01 to 2, particularly preferably 0.01 to 1. The alkali metal in this case is preferably sodium or potassium, in particular sodium. It is also possible to employ mixtures of several alkali metals.

The alkali metal is preferably present on a spinel or inverse spinel of the formulae (I) or (II)

where

A is divalent metal,

B is tri- or tetravalent metal,

X is O, S, Se, halogen, pseudohalogen, as carrier. The charges are moreover balanced. The spinels or inverse spinels employed as carriers are known per se. They are described, for example, in Holleman, Wiberg, Lehrbuch der anorganischen Chemie, Walter de Gruyter-Verlag, 101st edition, 1995, page 1061.

A is preferably selected from Mg, Cr, Fe, Zn, Mn, Co, Ni, Cu, Cd, Sn and mixtures thereof, and B is preferably selected from Al, Ga, In, Fe, V, Cr, Ti, Pb, Mn, Co, Rh, Ni, Si and mixtures thereof. X is preferably O.

The carrier is preferably selected from Mg/Al, Co/Al/Pb/Zn, Co/Ni/Fe/Cr, Co/Zn, Cr/Zn/Co/Si, Cu/Zn/Al and Cu/Al spinels.

Mg/Al and Co/Al/Pb/Zn spinels are particularly preferred. In the Mg/Al spinets the Al content is preferably 20–50, in particular 26–45, and the Mg content is 10–20, in particular 14–15, %, and the alkali metal content is 3–8, in particular 4.5 to 6, % of the total weight of the spinel. In a Co/Al/Pb/Zn spinel there are preferably 15–25% by weight of Co and 3–6% by weight of each of Pb and Zn in addition. The carrier can furthermore be doped with at least one compound of an alkali metal and/or alkaline earth metal in the dopant/carrier ratio by weight of from 0.01 to 5, preferably 0.01 to 2, in particular 0.01 to 1. The catalyst is preferably doped in this way. The doping of the carrier is preferably carried out with soluble compounds of the alkali metals and/or alkaline earth metals, such as the oxides, hydroxides, carbonates, formates, acetates, oxalates and/or hydrides. The hydroxides or carbonates are preferably employed, particularly preferably $K_2CO_3$ and/or KOH.

Preparation of the catalysts

The catalysts are prepared by applying at least one alkali metal to the carrier of the formulae (I) or (II) by applying molten alkali metal to the carrier or impregnating the carrier with solutions of an alkali metal azide, drying the carrier and decomposing the alkali metal azide or vapor-depositing the alkali metal on the carrier or impregnating the carrier with ammoniacal solutions of the alkali metal and removing the ammonia, where the carrier of the formulae (I) or (II) has, where appropriate, been previously doped by impregnating with a solution of at least one compound of an alkali metal and/or alkaline earth metal, drying and cacining the doped carrier.

The doping takes place in a conventional way by impregnating and subsequently calcining at from 200 to 1500° C., preferably 250 to 1000° C., particularly preferably 250 to 900° C. It is moreover possible for the impregnation to take place with a solution of the compound of the alkali metal and/or alkaline earth metal in any suitable solvent. Aqueous solutions are preferably employed, in which case the water is removed after the impregnation by drying the impregnated carrier. Calcination is also possible without previous drying, in which case the solvent escapes at the start of the calcination. The doped carrier can be calcined under reduced pressure, under atmospheric pressure or under elevated pressure. It can moreover take place either in an oxygen-containing atmosphere, or in an inert gas atmosphere, such as under helium, nitrogen or argon, or under a reactive gas atmosphere, such as under hydrogen, ammonia, carbon dioxide or carbon monoxide.

The alkali metals are applied to the, preferably doped, carriers in a conventional way. This includes application to the carrier in the molten state at from 100 to 300° C., as described, for example, in GB-A-1 143 993. To do this, the appropriate amount of the alkali metal is added as extrudate or block to the carrier and mixed with it while heating. During this, the alkali metal is finely dispersed on the carrier. It is furthermore possible to prepare the alkali metals by impregnating with solutions of alkali metal azides and then thermally decomposing the azides. A corresponding process is described, for example, in FR-A-2 609 024. The alkali metals can also be applied to the carrier by vapor deposition. This usually takes place under reduced pressure.

It is furthermore possible for the carriers to be impregnated with ammoniacal solutions of alkali metals, and the ammonia can then be evaporated. The application of alkali metals to the carrier preferably takes place under reduced pressure or under an inert gas atmosphere, such as under helium, nitrogen, hydrogen or argon.

The catalysts are employed in reactions catalyzed by strong bases, preferably for the side-chain alkylation or side-chain alkenylation of alkylaromatic or alkylalicyclic compounds with olefins or diolefins, for double-bond isomerization of olefins or for dimerization of olefins.

The reaction in these cases is generally carried out at from −50 to 400° C., preferably from −20 to 300° C., particularly preferably 80 to 250° C., in particular 100 to 220° C., under a pressure of, preferably, from 0.1 to 200, particularly preferably 1 to 150, in particular 1 to 100, bar.

The alkylaromatic compounds which can be employed are all suitable alkylaromatic compounds. They may have as aromatic nucleus, for example, a benzene or naphthalene nucleus. Also suitable are alkylalicyclic compounds in which the cyclic nucleus may be a cyclic alkyl, alkenyl or alkynyl radical. It is also possible to employ radicals in which there are several ring structures linked together. The ring structures have an acidic hydrogen atom in the α position of the side chain. They preferably have at least one alkyl radical which is bonded to the cyclic structure. The alkyl radicals can in these cases have any length and be substituted by further substituents. The alkylaromatic compounds employed are preferably benzenes substituted by 1 to 6, preferably 1 to 3, in particular 1 to 2, $C_{1-20}$, preferably $C_{1-3}$, alkyl radicals, or naphthalenes substituted by 1 to 10, preferably 1 to 5, particularly preferably 1 to 2, $C_{1-20}$, preferably $C_{1-3}$, alkyl radicals, and the alkylalicyclic compounds employed are preferably cyclopentenes or cyclohexenes respectively substituted by 1 to 5, preferably 1 or 2, or 1 to 6, preferably 1 to 3, in particular 1 or 2, $C_{1-20}$, preferably $C_{1-3}$, alkyl radicals.

The olefins preferably have 2 to 20, particularly preferably 2 to 10, in particular 2 to 5, carbon atoms. Ethene, propene, 1-butene, 2-butene, isobutene, 1-pentene, 2-pentene, 2-methyl-1-butene, 2-methyl-2-butene and/or 3-methyl-1-butene are preferably employed. Ethene and propene are particularly preferred. The diolefins preferably have 4 to 20, particularly preferably 4 to 10, in particular 4 to 6, carbon atoms. Butadiene and/or isoprene are particularly preferably employed.

Particularly preferred reactions are that of toluene with ethene or propene to give propylbenzene or isobutylbenzene, that of cumene with ethene to give tert-amylbenzene, and that of xylenes with butadiene to give 5-tolylpentenes.

The reaction can be carried out batchwise or, preferably, continuously in is the liquid or gas phase, preferably in the liquid phase. The process can be carried out in conventional apparatus.

The invention is illustrated further by means of examples hereinafter.

EXAMPLES

Preparation Examples

The elemental analyses per 100 g of the doped carrier before application of the alkali metal are indicated in parentheses after each example.

Catalyst A (comparative)

γ-$Al_2O_3$ was impregnated with 10% by weight $K_2CO_3$ (dissolved in $H_2O$). The suspension was evaporated to dryness, and the resulting powder was calcined in a stream of air at 500° C. The material was then stirred dry at 300° C. under reduced pressure for 3 h. 10% by weight metallic sodium were added to this powder and dispersed at 300° C. (Al 44.5 g; K 5.9 g).

Catalyst B

Mg/Al spinel from Baikowski, Nancy, France, was impregnated with 10% by weight $K_2CO_3$ (dissolved in $H_2O$). The suspension was evaporated to dryness, and the resulting powder was calcined in a stream of air at 500° C. The material was then stirred dry at 300° C. under reduced pressure for 3 h. 10% by weight metallic sodium were added to this powder and dispersed at 300° C. (Al 33 g; Mg 14.6 g; K 5 g).

Catalyst C

Mg/Al spinel (Baikowski) was impregnated with 10% by weight NaOH (dissolved in $H_2O$). The suspension was evaporated to dryness, and the resulting powder was calcined in a stream of air at 500° C. The material was then stirred dry at 300° C. under reduced pressure for 3 h. 10% by weight metallic potassium were added to this powder and dispersed at 300° C. (Al 34 g; Mg 14.6 g; Na 5.7 g).

Catalyst D

Mg/Al spinel (Baikowski) was impregnated with 10% by weight KOH (dissolved in $H_2O$). The suspension was evaporated to dryness, and the resulting powder was calcined in a stream of air at 500° C. The material was then stirred dry at 300° C. under reduced pressure for 3 h. 10% by weight metallic potassium were added to this powder and dispersed at 300° C. (Al 35 g; Mg 14.7 g; K 4.5 g).

Catalyst E

Mg/Al spinel (Baikowski) was impregnated with 10% by weight KOH (dissolved in $H_2O$). The suspension was evaporated to dryness, and the resulting powder was calcined in a stream of air at 500° C. The material was then stirred dry at 300° C. under reduced pressure for 3 h. 10% by weight metallic sodium were added to this powder and dispersed at 300° C. (Al 35 g; Mg 14.7 g; K 4.5 g).

Catalyst F

Mg/Al spinel (Baikowski) was impregnated with 10% by weight CsNO$_3$ (dissolved in H$_2$O). The suspension was evaporated to dryness, and the resulting powder was calcined in a stream of air at 500° C. The material was then stirred dry at 300° C. under reduced pressure for 3 h. 10% by weight metallic sodium were added to this powder and dispersed at 300° C. (Al 36.5 g; Mg 14.8 g; Cs 5 g).

Catalyst G

Co/Al/Pb/Zn spinel (manufactured by BASF AG, Ludwigshafen) was impregnated with 10% by weight KOH (dissolved in H$_2$O). The suspension was evaporated to dryness, and the resulting powder was calcined in a stream of air at 500° C. The material was then stirred dry at 300° C. under reduced pressure for 3 h. 10% by weight metallic sodium were added to this powder and dispersed at 300° C. (Al 26.5 g; Co 20.3 g; K 5.5 g; Pb 4.6 g; Zn 4.6 g).

Catalyst H

Co/Ni/Fe/Cr spinel (BASF) was impregnated with 10% by weight KOH (dissolved in H$_2$O). The suspension was evaporated to dryness, and the resulting powder was calcined in a stream of air at 500° C. The material was then stirred dry at 300° C. under reduced pressure for 3 h. 10% by weight metallic sodium were added to this powder and dispersed at 300° C. (Fe 24 g; Cr 23.6 g; Co 6.8 g; Ni 9.4 g; K 5.7 g).

Catalyst J

Co/Zn spinel (BASF) was impregnated with 10% by weight KOH (dissolved in H$_2$O). The suspension was evaporated to dryness, and the resulting powder was calcined in a stream of air at 500° C. The material was then stirred dry at 300° C. under reduced pressure for 3 h. 10% by weight metallic sodium were added to this powder and dispersed at 300° C. (Zn 59 g; Co 10 g; K 5.4 g).

Catalyst K

Co/Zn/Cr/Si spinel (BASF) was impregnated with 10% by weight KOH (dissolved in H$_2$O). The suspension was evaporated to dryness, and the resulting powder was calcined in a stream of air at 500° C. The material was then stirred dry at 300° C. under reduced pressure for 3 h. 10% by weight metallic sodium were added to this powder and dispersed at 300° C. (Cr 37 g; Zn 10.5 g; Co 6.9 g; Si 6.2 g; K 5.6 g).

Catalyst L

Cu/Zn/Al spinel was impregnated with 10% by weight KOH (dissolved in H$_2$O). The suspension was evaporated to dryness, and the resulting powder was calcined in a stream of air at 500° C. The material was then stirred dry at 300° C. under reduced pressure for 3 h. 10% by weight metallic sodium were added to this powder and dispersed at 300° C. (Al 29.4 g; Cu 10.6 g; Zn 13.8 g; K 5.4 g).

Catalyst M

Cu/Al spinel was impregnated with 10% by weight KOH (dissolved in H$_2$O). The suspension was evaporated to dryness, and the resulting powder was calcined in a stream of air at 500° C. The material was then stirred dry at 300° C. under reduced pressure for 3 h. 10% by weight metallic sodium were added to this powder and dispersed at 300° C. (Al 36 g; Cu 13.4 g; K 4.6 g).

Catalyst N

The spinel employed was the same as for catalyst D. However, the calcination took place at 250° C.

Catalyst O

The spinel employed was the same as for catalyst E. However, the calcination took place at 250° C.

Catalyst P

The spinel employed was the same as for catalyst E. However, the calcination took place at 600° C.

Catalyst Q

The spinel employed was the same as for catalyst E. However, the calcination took place at 700° C.

Catalyst R

The spinel employed was the same as for catalyst E. However, the calcination took place at 800° C.

Process examples

Comparative Example C1

10 g of catalyst A were introduced with 85 g of toluene into a pressure-resistant reaction vessel. 20 g of propene were added and then the reaction vessel was heated to 160° C. and the suspension was stirred for 12 h. The results are listed in Table 1.

Examples 1–16

10 g of catalysts B to R were in each case introduced with 85 g of toluene into a pressure-resistant reaction vessel. 20 g of propene were added and then the reaction vessel was heated to 160° C. and the suspension was stirred for 12 h. The results are listed in Table 1.

TABLE 1

| | Catalyst | $U_{propene}$ | $S_{iBB}$ | $S_{BB}$ | MP | MI |
|---|---|---|---|---|---|---|
| Comparative Example C1 | A | 34% | 66% | 70% | 5.7% | 0.2% |
| Example 1 | B | 42% | 77% | 86% | 2.6% | 1.5% |
| Example 2 | C | 37% | 81% | 86% | 1.6% | 1.1% |
| Example 3 | D | 50% | 80% | 89% | 2.6% | 0.1% |
| Example 4 | E | 22% | 73% | 79% | 1.9% | 0.7% |
| Example 5 | F | 16% | 78% | 88% | 1.0% | 0.2% |
| Example 6 | G | 60% | 78% | 87% | 3.3% | 0.3% |
| Example 7 | H | 30% | 80% | 89% | 1.5% | 0.1% |
| Example 8 | J | 20% | 71% | 81% | 1.8% | 0.1% |
| Example 9 | K | 13% | 72% | 79% | 1.4% | 0.4% |
| Example 10 | L | 35% | 74% | 82% | 3.3% | 0.1% |
| Example 11 | M | 22% | 68% | 75% | 2.4% | 0.1% |
| Example 12 | N | 50% | 81% | 90% | 2.4% | 0.1% |
| Example 13 | O | 28% | 77% | 82% | 1.6% | 1.2% |
| Example 14 | P | 20% | 80% | 85% | 1.0% | 0.8% |
| Example 15 | Q | 35% | 74% | 79% | 2.3% | 1.7% |
| Example 16 | R | 34% | 74% | 79% | 2.6% | 1.4% |

$U_{propene}$ = Propene conversion [mol %]
$S_{iBB}$ = Selectivity for isobutylbenzene [mol %]
$S_{BB}$ = Selectivity for iso- and n-butylbenzene [mol %]
MP = Methylpentene, % by weight in the discharge
MI = Methylindan, % by weight in the discharge Comparative Example C2

20 g of catalyst were introduced with 100 g of toluene into a pressure-resistant reaction vessel (volume 150 ml) and heated to 160° C. Then a mixture of toluene and propene (toluene:propene molar ratio=2:1) was metered continuously (6 ml/h) into the reaction vessel. The pressure was kept at 50 bar. Table 2 shows the results. The methylpentene discharge rose continuously and did not cease until the reaction was stopped.

TABLE 2

| % by weight | Time (h) | | | | | | | | | | | |
|---|---|---|---|---|---|---|---|---|---|---|---|---|
| | 18 | 25 | 36 | 45 | 49 | 57 | 69 | 73 | 81 | 89 | 93 | 97 |
| Isobutylbenzene | 9.5 | 11.7 | 12.3 | 12.2 | 12.7 | 12.3 | 12.2 | 12.4 | 12.2 | 12.4 | 12.3 | 12.0 |
| n-Butylbenzene | 0.6 | 0.63 | 0.63 | 0.61 | 0.62 | 0.60 | 0.58 | 0.59 | 0.57 | 0.58 | 0.57 | 0.54 |
| Methylpentene | 0.56 | 0.88 | 1.27 | 1.59 | 1.81 | 2.00 | 2.34 | 2.49 | 2.79 | 2.99 | 3.32 | 3.60 |
| Methylindan | 0.13 | 0.16 | 0.21 | 0.24 | 0.26 | 0.27 | 0.28 | 0.30 | 0.31 | 0.32 | 0.33 | 0.34 |

Example 12

20 g of catalyst B were introduced with 100 g of toluene into a pressure-resistant reaction vessel (volume 150 ml) and heated to 160° C. Then a mixture of toluene and propene (toluene:propene molar ratio=2:1) was metered continuously (6 ml/h) into the reaction vessel. The pressure was kept at 50 bar. Table 3 shows the results. The isobutylbenzene yield was larger, and the amount of byproducts formed was significantly less, than in Comparative Example C2.

TABLE 3

| % by weight | Time (h) | | | | | | | | | | | | | |
|---|---|---|---|---|---|---|---|---|---|---|---|---|---|---|
| | 49 | 54 | 62 | 70 | 78 | 86 | 98 | 106 | 126 | 130 | 138 | 148 | 153 | 161 |
| Isobutylbenzene | 10.1 | 13.0 | 14.8 | 15.9 | 17.4 | 18.6 | 19.4 | 21.8 | 23.2 | 26.9 | 26.8 | 25.70 | 26.00 | 25.40 |
| n-Butylbenzene | 0.74 | 0.90 | 0.98 | 1.02 | 1.07 | 1.11 | 1.12 | 1.25 | 1.30 | 1.48 | 1.46 | 1.40 | 1.42 | 1.39 |
| Methylpentene | 0.49 | 0.54 | 0.74 | 0.85 | 0.98 | 1.18 | 1.40 | 1.42 | 1.75 | 2.24 | 2.14 | 2.21 | 2.32 | 2.37 |
| Methylindan | 0.6 | 0.9 | 1.0 | 1.1 | 1.3 | 1.4 | 1.5 | 1.8 | 1.8 | 2.1 | 2.1 | 2.0 | 2.0 | 2.0 |

We claim:

1. A catalyst comprising at least one alkali metal on a spinel or inverse spinel as carrier, which may be doped with at least one compound selected from the group consisting of oxides, hydroxides, carbonates, formates, acetates, oxalates, and/or hydrides of alkali metal and alkaline earth metal, where the alkali metal/carrier ratio by weight is from 0.01 to 5 and, when a dopant is present, the dopant/carrier ratio by weight is from 0.01 to 5.

2. A catalyst as claimed in claim 1, wherein the spinel has formula (I) and the inverse spinel has formula (II)

$$AB_2X_4 \quad (I)$$

$$B(AB)X_4 \quad (II)$$

where

A is divalent metal,

B is tri- or tetravalent metal,

X is O, S, Se, halogen, pseudohalgen, the charges being balanced.

3. A catalyst as claimed in claim 2, wherein A is selected from the group consisting of Mg, Cr, Fe, Zn, Mn, Co, Ni, Cu, Cd, Sn and mixtures thereof, and B is selected from the group consisting of Al, Ga, In, Fe, V, Cr, Ti, Pb, Mn, Co, Rh, Ni, Si and mixtures thereof, and X is O.

4. A catalyst as claimed in claim 1, wherein the carrier is selected from Mg/Al, Co/Al/Pb/Zn, Co/Ni/Fe/Cr, Co/Zn, Cr/Zn/Co/Si, Cu/Zn/Al and Cu/Al spinels.

5. A process for preparing a catalyst by applying at least one alkali metal to a spinel or inverse spinel carrier, wherein the spinel has formula (I) and the inverse spinel has formula (II)

$$AB_2X_4 \quad (I)$$

$$B(AB)X_4 \quad (II)$$

where

A is divalent metal,

B is tri- or tetravalent metal,

X is O, S, Se, halogen, pseudohalogen, the charges being balanced, by applying molten alkali metal to the carrier or impregnating the carrier with solutions of an alkali metal azide, drying the carrier and decomposing the alkali metal azide or vapor-depositing the alkali metal on the carrier or impregnating the carrier with ammoniacal solutions of the alkali metal and removing the ammonia, where the carrier of the formulae (I) or (II) has, where appropriate, been previously doped by impregnating with a solution of at least one compound selected from the group consisting of oxides, hydroxides, carbonates, formates, acetates, oxalates, and/or hydrides of alkali metal and alkaline earth metal, drying and calcining the doped carrier.

* * * * *